United States Patent [19]

Eisen et al.

[11] Patent Number: 4,772,557

[45] Date of Patent: Sep. 20, 1988

[54] DNA CLONE OF HUMAN SKIN FIBROBLAST COLLAGENASE ENZYME

[75] Inventors: Arthur Z. Eisen; Gregory I. Goldberg; Eugene A. Bauer, all of St. Louis, Mo.

[73] Assignee: Washington University, St. Louis, Mo.

[21] Appl. No.: 797,262

[22] Filed: Nov. 12, 1985

[51] Int. Cl.⁴ .................. C12N 1/00; C12N 15/00; C12N 9/64; C07H 17/00

[52] U.S. Cl. .................. 435/320; 435/172.3; 435/226; 536/27; 935/14

[58] Field of Search .............. 435/172.3, 226, 212, 435/91, 320; 935/6, 14; 536/27

[56] References Cited

PUBLICATIONS

Alexander, D. et al., *Gene,* vol. 31, pp. 79–89, Nov., 1984.

Okayama, H. et al., *Molec. and Cell. Biol.,* vol. 2, pp. 161–170, 1982.

Goldberg, G. et al., *J. Biol. Chem,* vol. 261, pp. 6600–6605, May, 1986.

Whitham, S. et al., *J. Biochem,* vol. 240, pp. 913–916, Dec., 1986.

Stricklin et al., *Biochemistry* 16, 1607–1615 (1977).

Stricklin et al., *Biochemistry* 17, 2331–2337 (1978).

Tyree et al., *Arch. Biochem. Biophys.* 208, 440–443 (1981).

Stricklin et al., *Biochemistry* 22, 61–68 (1983).

Welgus et al., *J. Biol. Chem.* 256, 9511–9515 (1981).

Matrisian et al., *EMBO Journal* 4, 1435–1440 (1985).

*Primary Examiner*—Thomas G. Wiseman
*Assistant Examiner*—Jayme A. Huleatt
*Attorney, Agent, or Firm*—Scott J. Meyer; James W. Williams, Jr.

[57] ABSTRACT

A cDNA having a base sequence for human skin fibroblast collagenase has been cloned and characterized and the amino acid sequence of the human skin fibroblast protein has been determined.

3 Claims, 2 Drawing Sheets

FIG. 2.

DNA CLONE OF HUMAN SKIN FIBROBLAST COLLAGENASE ENZYME

BACKGROUND OF THE INVENTION

This invention relates to human skin fibroblast collagenase and, more particularly, to the cDNA clone representing the full size human skin fibroblast collagenase mRNA.

Collagens constitute the most abundant proteins of the extracellular matrix in mammalian organisms. Though collagen turnover is generally very slow, its metabolism intensifies dramatically concomitant with processes requiring remodeling of the connective tissue, such as uterine involution, bone resorption, and wound healing. Enhanced collagen metabolism has also been implicated in the pathogenesis of a number of diseases which include recessive dystrophic epidermolysis bullosa, rheumatoid arthritis, corneal and gingival disease. The initiation of the dismantling of an existing collagen network requires specific enzymes, designated collagenases, which catalyze the initial step in the proteolytic degradation of collagen.

Several types of collagenase can be distinguished based on their physical properties and substrate specificity for different types of collagen. Collagenases degrading the interstitial collagens, types I, II and III, do not cleave collagen types IV and V, which apparently are degraded by other proteases. The structural relationship among these functionally different collagenases has not yet been determined. The interstitial collagenases from human skin synovium, gingiva and monocytes comprise a group of metalloendoproteases which generally appear to be similar. Human granulocyte collagenase, which also degrades interstitial collagens, differs from the other interstitial collagenases immunologically, in substrate preference, and in molecular weight, indicating that tissue differences in human interstitial collagenases exist. All these enzymes catalyze a single specific cleavage in each of the three collagen polypeptide chains, thereby rendering the collagen fiber soluble, thermally unstable and susceptible to attack by specific gelatinases and probably by other tissue proteases.

Collagenase from human skin fibroblasts has been purified as described by Stricklin et al., Biochemistry 16, 1607-1615 (1977), Ibid., 17, 2331-2337 (1978). The proenzyme is secreted as two closely related polypeptides reported to have apparent molecular weight of 60 kilodaltons (kDA) and 55 kDA, respectively. Both enzyme forms can be activated by several different mechanisms to produce active enzyme. See Tyree et al., Arch. Biochem. Biophys. 208, 440-443 (1981) and Stricklin et al., Biochemistry 22, 61-68 (1983). Collagenase from human skin fibroblasts also has been characterized enzymatically by Welgus et al., J. Biol. Chem. 256, 9511-9515 (1981).

Further background information on mammalian collagenase can be had by reference to a treatise such as, for example, Collagenase in Normal and Pathological Connective Tissues, Woolley and Evanson, Eds., John Wiley & Sons, New York, N.Y., 1980.

Recent advances in biochemistry and in recombinant DNA technology have made it possible to synthesize specific proteins, for example, enzymes, under controlled conditions independent of the organism from which they are normally isolated. These biochemical synthetic methods employ enzymes and subcellular components of the protein synthesizing systems of living cells, either in vitro in cell-free systems, or in vivo in microorgamisms. In either case, the principal element is provision of a deoxyribonucleic acid (DNA) of specific sequence which contains the information required to specify the desired amino acid sequence. Such a specific DNA sequence is termed a gene. The coding relationships whereby a deoxyribonucleotide sequence is used to specify the amino acid sequence of a protein is well-known and operates according to a fundamental set of principles. See, for example, Watson, Molecular Biology of the Gene, 3d ed., Benjamin-Cummings, Menlo Park, Calif., 1976.

A cloned gene may be used to specify the amino acid sequence of proteins synthesized by in vitro systems. DNA-directed protein synthesizing systems are well-established in the art. Single-stranded DNA can be induced to act as messenger RNA (mRNA) in vitro, thereby resulting in high fidelity translation of the DNA sequence.

It is now possible to isolate specific genes or portions thereof from higher organisms, such as man and animals, and to transfer the genes or fragments to microorganisms such as bacteria or yeasts. The transferred gene is replicated and propogated as the transformed microorganism replicates. Consequently, the transformed microorganism is endowed with the capacity to make the desired protein or gene which it encodes, for example, an enzyme, and then passes on this capability to its progeny. See, for example, Cohen and Boyer, U.S. Pat. Nos. 4,237,224 and 4,468,464.

BRIEF DESCRIPTION OF THE INVENTION

In accordance with the present invention, the complete coding sequence of the cDNA clone complementary to the full size human skin fibroblast collagenase mRNA has been developed. The clone, pCol 185.2, contains a 1970 base pair (bp) insert excluding the oligo (G) and poly (A) tails. The identification of the clone is based on its colinearity with a single mRNA specie coding for both the sequence of the peptide isolated from a purified collagenase preparation and the sequence of the amino termini of both the 47 kDa and 42 kDa activated enzyme forms.

The original source of the genetic material was normal adult human skin fibroblasts. Such cells are readily available from ordinary skin biopsies and any normal adult human skin fibroblasts can be used as source materials. A preferred source illustrated herein is the normal adult human skin fibroblast cell strain designated WUN 80547. The cell line WUN 80547 is available from the Division of Dermatology, Washington University School of Medicine, St. Louis, Mo. Other suitable cells lines are, for example, the normal human skin fibroblast cell lines available from the American Type Culture Collection, Rockville, Md. Typical of such cell lines, are the ones designated ATCC CRL 1187 (Robel) and ATCC CRL 1224 (Le Mor).

The clone, pCol 185.2, has coding capacity for all the peptides isolated and sequenced from the purified collagenase preparation.

In the full sequence of the clone, the 68 bp of the 5' untranslated region is followed by the initiating Met codon. The open translation frame extends for 1407 bp, coding for 469 amino acids of the preprocollagenase protein with the $M_r$ 54,092. The first 19 amino acids of the open translation frame constitutes the signal peptide and the mature proenzyme protein begins with Phe at position 20, giving a proenzyme of $M_r$ 51,929. The 492 bp following the first TGA termination codon represents the 3' untranslated end of the mRNA.

The human skin fibroblast collagenase described herein has potential use in treatment of hypertrophic scars, keloids and intervertebral disc disease.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention in conjunction with the appended drawings, in which briefly:

FIG. 2 shows the nucleotide sequence of human skin fibroblast collagenase cDNA and the amino acid sequence of the human skin fibroblast protein.

Figure 1:
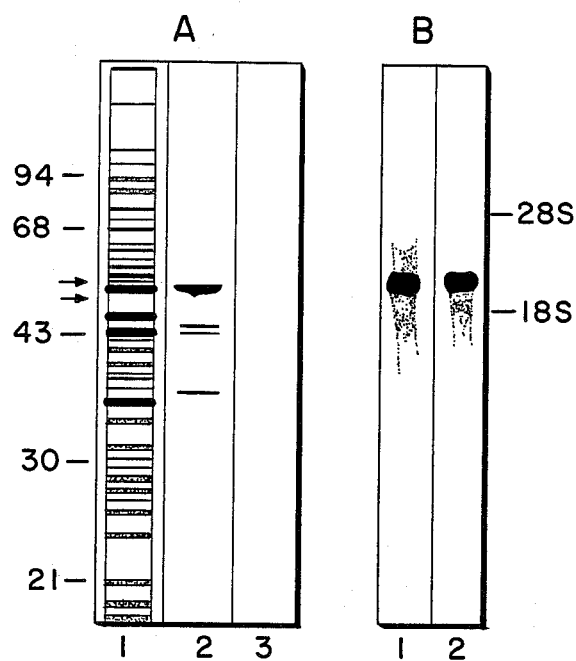
FIG. 1 shows the cell free translation and Northern blot analysis of mRNA derived from human skin fibroblasts.

Standard biochemical nomenclature is used herein in which the nucleotide bases are designated as adenine (A); thymine (T), guanine (G), and cytosine (C). Amino acids are shown either by three letter or one letter abbreviations as follows:

| Abbreviated Designation | | Amino Acid |
| --- | --- | --- |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Other standard abbreviations used are:
deoxyadenosine triphosphate (dATP);
deoxyguanosine triphosphate (dGTP);
deoxycytidine triphosphate (dCTP);
thymidine triphosphate (TTP).

In order to illustrate specific preferred embodiments of the invention in greater detail, the following exemplary laboratory preparative work was carried out:

EXAMPLE (a) Cell culture, enzyme purification and preparation of cytoplasmic RNA Conditioned medium from normal adult human skin fibroblasts (WUN 80547 cell strain) was collected every 48-72 hours and procollagenase was purified according to the method described previously by Stricklin et al., *Biochemistry* 16, 1607-1615 (1977). According to this procedure, the cells were grown at 37° C. in Dulbecco's modified Eagle's medium supplemented with 20% fetal bovine serum and purification of the conditioned medium was carried out using a combination of cation exchange with carboxymethylcellulose and gel filtration chromatography with Sephadex ® G-100 or Ultragel ® AcA-44. Collagenase protein was then measured by indirect enzyme-linked immunosorbent assay (ELISA). See Cooper et al., *Collagen Rel. Res.* 3, 205-216 (1982). Fresh medium was added to 70% confluent cell cultures 24 hours before harvesting for RNA isolation. Total cytoplasmic RNA from the harvested fibroblast cells was isolated essentially as described by Sperling et al., *Mol. Cell. Biol.* 5, 569-575 (1985). Poly (A)+RNA was prepared by oligo(dT)-cellulose chromatography [See Aviv et al., *Proc. Natl. Acad. Sci. USA* 69, 1408-1412 (1972)] and used in a reticulocyte lysate cell-free translation system, Northern blot analysis, primer extension reactions and construction of a cDNA library.

(b) Protein sequencing

An S-carboxymethylated preparation of human skin fibroblast collagenase was subjected to cyanogen bromide cleavage or trypsin digestion by procedures as previously described by Grant et al., *Biochemistry* 19, 4653-4659 (1980). Cyanogen bromide peptides were separated by High Performance Liquid Chromatography (HPLC) on a Varian 5000 HPLC using a 4.6 mm×25 cm Beckman-Altex ODS (5μ) reverse phase column, equilibrated in 0.05% trifluoroacetic acid (TFA) and developed with linear gradients of acetonitrile (1%, 0.5% or 0.25%/min) in 0.05% trifluoroacetic acid or in a gradient of 0.5%/min isopropanol. Peptides produced by digestion with trypsin were fractionated using the same system with similar gradients and a 3.9 mm×30 cm Waters C-18 microbondapak column. Sequence analysis of polypeptides was performed by automated Edman degradation on either a Beckman 890C spinning cup sequencer using a standard 0.33 M Quadrol program or on an Applied Biosystems 470 A gas phase sequencer. The phenylthiohydantoins, after conversion from the phenylthiazolinones, were identified by reverse phase HPLC on a Beckman-Altex Ultrasphere ODS-PTH column. See Grant et al., *Biochemistry* 22, 354-358 (1983). Alternatively, enzyme preparations (100-300 μg) were size fractionated on sodium dodecylsulfate polyacrylamide gel electrophoresis (NaDodSO4/PAGE). The proteins were electroblotted onto an activated glass fiber sheet and stained with Coomassie blue. The protein bands were cut out from the blot and placed directly in the cartridge of the gas phase sequencer.

(c) Primer extension reaction

Five micrograms of mRNA and 0.1-0.5 pmol of =P end labeled synthetic oligonucleotide primer in 0.1 ml of 0.1 M NaCl, 10 mM Tris-HCl, pH 7.5, 1 mM ethylenediamine tetracetate (EDTA) (Buffer A) was extracted with phenol-chloroform-isoamyl alcohol (49:49:2) and precipitated with ethanol. The pellet was dried, resuspended in 5 μl of 1 M NaCl, 0.1 M piperazine-N,N'-bis[2-ethanesulfonic Acid] (PIPES), pH 6.4, 2.5 mM EDTA and the primer annealed to mRNA for 3 hours at 40° C., a temperature slightly below the Tm (temperature at which 50% of the DNA duplex melts) for the primers SO3 and SO6 (Table II). At the end of the hybridization, 5 μl of buffer containing 250 mM Tris-base, 80 mM MgCl$_2$, 4 mM dithiothreitol (DTT) was added. Then 5 μl of a 10 mM solution of each dATP, dGTP, dCTP and TTP, and 33 μl H$_2$O was added and the pH of the mixture adjusted to 8.3. Reverse transcriptase (Life Sciences) was added to obtain a concentration of 10 U/μg of mRNA. The mixture was incubated for 1 hr at 42° C. and the reaction was stopped by addition of 150 μl of Buffer A and 2 μl of 10% Na DodSO$_4$. The reaction mixture was extracted with phenol-chloroform and RNA was hydrolyzed by addition of NaOH to a final concentration of 0.5M. After hydrolysis for 0.5 hour at room temperature the reaction mixture was neutralized and precipitated with ethanol. The dry pellet was resuspended in formamide and electrophoresed on a denaturing 8% polyacrylamide-8.3M urea gel. Reaction products were isolated from the gel and sequenced using the partial chemical degradation method of Maxam and Gilbert, *Proc. Natl. Acad. Sci. USA*, 74, 560–564 (1977).

(d) Construction of cDNA library

Human skin fibroblast mRNA was used to construct a cDNA library using a modification of the Okayama and Berg procedure, *Mol. Cell. Biol.* 3, 280–289 (1983), as described by Alexander et al., *Gene* 31, 79–89 (1984). The library represents 1.5×10$^6$ original cloning events obtained from 12 μg of mRNA. The transformants were amplified on agar plates containing 100 μg/ml of ampicillin. The colonies were scraped from the plates and grown in M9 media supplemented with 0.2% casaminoacids for two generation times. The total library plasmid DNA was isolated and size fractionated on 1% agarose gel in a supercoiled form essentially by procedure described by Kahn et al., *Methods in Enzymology* 68, 268–280 (1979). The fractions of supercoiled DNA migrating above the supercoiled vector were extracted from the gel and used to retransform host bacteria. Transformants obtained from the fraction containing inserts of the desired size range were plated at 10$^4$ colonies/100 cm$^2$ square petri dish and screened for hybridization with synthetic oligonucleotides by methodology described by Hanahan & Meselson, *Gene* 10, 63–67 (1980).

(e) Northern blot analysis of RNA

A total mRNA preparation (5 μg) was fractionated on 1.2% agarose gel containing 2.2M formaldehyde and transferred to nitrocellulose filters. For these general procedures, see, respectively, Maniatis et al., *Molecular Cloning: A Laboratory Manual*, Cold Spring Harbor Laboratory, Cold Spring Harbor, N.Y., 1982, at pp. 202–203; and Thomas, *Proc. Natl. Acad. Sci. USA* 77, 5201–5205 (1980).

(f) Hybridization conditions $^{32}$P End-labeled synthetic oligonucleotides (17 bases long), 1×10$^6$ cpm/ml, were hybridized to nitrocellulose filters for 18–36 hours in a solution containing 0.9M NaCl/0.09M Na Citrate, 0.5% NaDodSO$_4$ or 0.5% NP-40 (Tergitol ® NP-40 nonionic surfactant, nonylphenol ethoxylate with average of 40 ethylene oxide units per molecule), 30 μg/ml of poly(A), 25 μg/ml of tRNA, 0.1% Ficoll, 0.1% BSA, 0.1% polyvinylpyrrolidone. Filters were washed 3 times in a solution of 0.45M NaCl/0.045M Na citrate, 0.1% NaDodSO$_4$ at room temperature for 5 min, once in a solution of 0.9M NaCl/0.09M Na citrate, 0.1% NaDodSO$_4$ at 40° C. for 2–5 min and twice with 0.45M NaCl/0.045M Na citrate, 0.1% NaDodSO$_4$ at room temperature.

Nick Translated plasmid DNA (1×10$^6$ cpm/ml) was hybridized to Northern blot for 18 hours at 42° C. in a solution of 50% formamide (v/v), 0.75M NaCl/0.075M Na citrate, 50 mM Na phosphate, pH 6.5, 0.1% Ficoll, 0.1% BSA, 0.1% polyvinylpyrrolidone, 0.1% NP-40, 30 μg/ml poly(A) (polyadenylic acid) and 50 μg/ml of denatured *E. coli* DNA. Filters were washed 2–3 times in 0.3 NaCl/0.03M Na citrate, 0.1% NP-40 for 5 min at room temperature and then 3 times for 5 min at 50° C. in 0.03M NaCl/0.003M Na citrate, 0.1% NP-40.

(g) Cell free translation 0.5–1 μg of mRNA was translated in a rabbit reticulocyte lysate cell free system (Promega Biotec) with 5 μl of $^{35}$S methionine (1070 Ci/mmole, 15 μCi/μl Amersham) in a 50 μl reaction mix to yield total incorporation of 2.5×10$^6$ cpm into TCA insoluble protein. Translation products were visualized after fractionation on 10% NaDodSO$_4$/PAGE and autoradiography. For these general procedures, see respectively, Laemmli, *Nature* 277, 680–685 (1970); and Bonner et al., *Eur. J. Biochem.* 46, 83–88 (1974). Immunoprecipitation with collagenase specific or nonimmune rabbit IgG was performed by general methodology as described previously by Clark et al., *Arch. Biochem. Biophys.* 241, 36–44 (1985).

Figure 3:
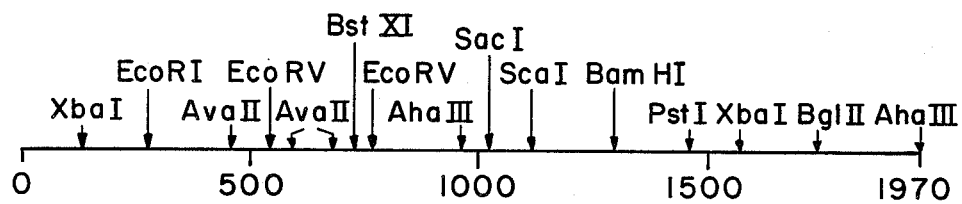
FIG. 3 shows the restriction enzyme map of the human skin fibroblast collagenase cDNA clone pCol 185.2

The results of the above laboratory preparative work leading to the identification of the single mRNA species coding for human skin fibroblast collagenase and clone pCol 185.2, which represents said complete mRNA coding sequence, are further exemplified by the following detailed description of FIGS. 1 to 3 of the drawings and Tables I to III, below.

FIG. 1

Cell free translation and Northern blot analysis of mRNA derived from human skin fibroblasts (A) One microgram of mRNA was translated in a rabbit reticulocyte lysate cell-free system. $^{35}$S Methionine-labeled proteins were size-fractionated on a 10% NaDodSO$_4$/PAGE before (lane 1) and after immunoprecipitation with collagenase-specific (lane 2) or nonimmune IgG (lane 3). The migration positions of the 57 kDa and 52 kDa procollagenase species are indicated by arrows. The numbers on the left represent molecular weight markers (Mr×10$^{-3}$).

(B) Five micrograms of mRNA were electrophoresed through a 1.2% agarose gel containing 2.2M formaldehyde blotted on a nitrocellulose filter and hybridized to the $^{32}$P end-labeled synthetic oligonucleotide SO3 (lane 1) or to nick-translated pCol 185.2 plasmid DNA (lane 2). Lane 1 was exposed 24 times longer than lane 2.

TABLE I

| | Amino acid sequence of the peptides derived from human skin procollagenase | |
|---|---|---|
| CN1 | KQXRCGVPDVAQFVLTEGNPXWEQT | 88–112 |
| CN2 | ISFVRGDHRDNSPFDGPGGNLAHAFQPGPGIGXDA<u>HFDEDE</u>XXTNNFR | 161–208 |

TABLE I-continued
Amino acid sequence of the peptides derived from human skin procollagenase

| | | |
|---|---|---|
| CN3 | YPSYTFSGDVQLAQDXIDGIQAIYG | 237-261 |
| CN4 | FFKDRFY | 296-302 |
| CN5 | XTNPFYPEVELNFISVFWPQLPNGLEAAYEFADXDEVXFFXGNKYWAVQGQNVLHGYP | 304-361 |
| CN6 | KDGFFYFFHGTRQYKFDP | 432-449 |
| TP1 | AFQLWSNVTPLTFTK | 137-151 |
| TP2 | VAAHELGXSLGLS | 215-227 |
| TP47, 42 | VLTEGNPR | 101-108 |

Peptides derived by cyanogen bromide cleavage (peptides CN 1–6) or trypsin digestion (peptides TP1, 2) of a purified preparation of procollagenase were separated and sequenced. The protein sequence of the amino-terminal portion of the 47 kDa and 42 kDa proteolytically activated collagenase species (peptides TP 47, 42) was obtained by sequencing the individual forms after separation by NaDodSO4/PAGE and electroblotting onto an activated glass fiber sheet. The numbers represent the positions of the amino and carboxy terminal amino acids of each peptide in the collagenase protein according to the nomenclature in FIG. 2 and Table III. The unidentified amino acid residues are designated as X. The underlined amino acid sequence of peptide CN2 was reverse translated to determine the sequence of the synthetic oligonucleotide SO3.

TABLE II
Nucleotide sequence of the synthetic oligonucleotide probes

| | | |
|---|---|---|
| S03 | TTCATCTTCATCAAAAT<br>  C  G      G G  G | 671-655 |
| S06 | CGTGTAATTTTCAATCC | 434-418 |

The synthetic oligonucleotides were synthesized using an Applied Biosystems DNA synthesizer. The sequence of probe SO3 was predicted by reverse translation of the amino acid sequence of peptide CN2 (Table I). The sequence of probe SO6 was obtained from the sequence of the SO3 primer extension product. The sequence of each probe is complementary to the coding strand sequence of the clone pCol 185.2 at the designated positions (FIG. 2).

FIG. 2

Nucleotide sequence of human skin collagenase cDNA

The sequence was determined and confirmed both strands using the partial chemical degradation method of Maxam and Gilbert, supra. The amino acid sequence of human skin collagenase based on the DNA sequence is shown under the DNA sequence. The putative site of the signal peptide cleavage is shown by an arrow. The amino-terminus of the proteolytically activated enzyme form is indicated by a star. Potential N-glycosylation sites are designated by boxes. Three cysteine residues and the potential poly(A) addition signal sequence are underlined.

TABLE III
Comparison of the amino acid sequences of human skin collagenase and the oncogene transformation induced rat protein of Matrisian, EMBO Journal 4, 1435-1440 (1985).

| | |
|---|---|
| MHSFPPLLLLLFWGVVSHSFPATLETQEQDVDLVQKYLEKYYNLKNDGRQ<br>    KGL V   W CT—A    S  Y LHGSEEDAGMEVL        N    G EK   VK | 50 |
| VEKRRNSGPVVEKLKQMQEFFGLKVTGKPDAETLKVMKQPRCGVPDVAQF<br>FT  KKD S     K  IQE     K L    M      L SN MEL  HK          GG | 100 |
| VLTEGNPRWEQTHLRYRIENYTPDLPRADVDHAIEKAFQLWSNVTPLTFT<br>STFP  S  K  RKN IS      V     L     ES    S     R LKV EE          S | 150 |
| KVSEGQADIMISFVRGDHRDNSPFDGPGGNLAHAFQPGPGIGGDAHFDED<br>RI     E           AVEE  G FI          MV       YA    TN          D | 200 |
| ERWTNNFREYNLHRVAAHELGHSLGLSHSTDIGALMYPSYTFSGDVQ——<br>       DDVTGT   FL         F       F   ANAE        V KS T   LARFH | 247 |
| LAQDDIDGIQAIYGRSQNPVQP—————IGPQTPKACDSKLTFDAIT<br>     S    V    SL    PPTESPDVLVVPTKSNSLD E  LPM S  A S       VS | 288 |
| TIRGEVMFFKDRFYMRTNPFYPEVELNFISVFWPQLPNGLEAAYEFADRD<br>    L     L       HFW  KSLRT   PGFYL  S      S    SNMD       VTD | 338 |
| EVRFFKGNKYWAVQGQNVLHGYPKDIYSSFGFPRTVKHIDAALSEENTGK<br>T  FIL      QI      IR   HEE   A       S HTL—L E      QK       I  LKDQK | 388 |
| TYFFVANKYWRYDEYKRSMDPSYPKMIAHDFPGIGHKVDAVFMKDGFFYF<br>       ED  F     F    K Q       EF RK    EN        T           EAF   L | 438 |
| FHGTRQYKFDPKTKRILTLQKANSWFNCRKN<br>   S  SS  LE      NAGKVTHIL  S        —— | 469 |

Figure 2:
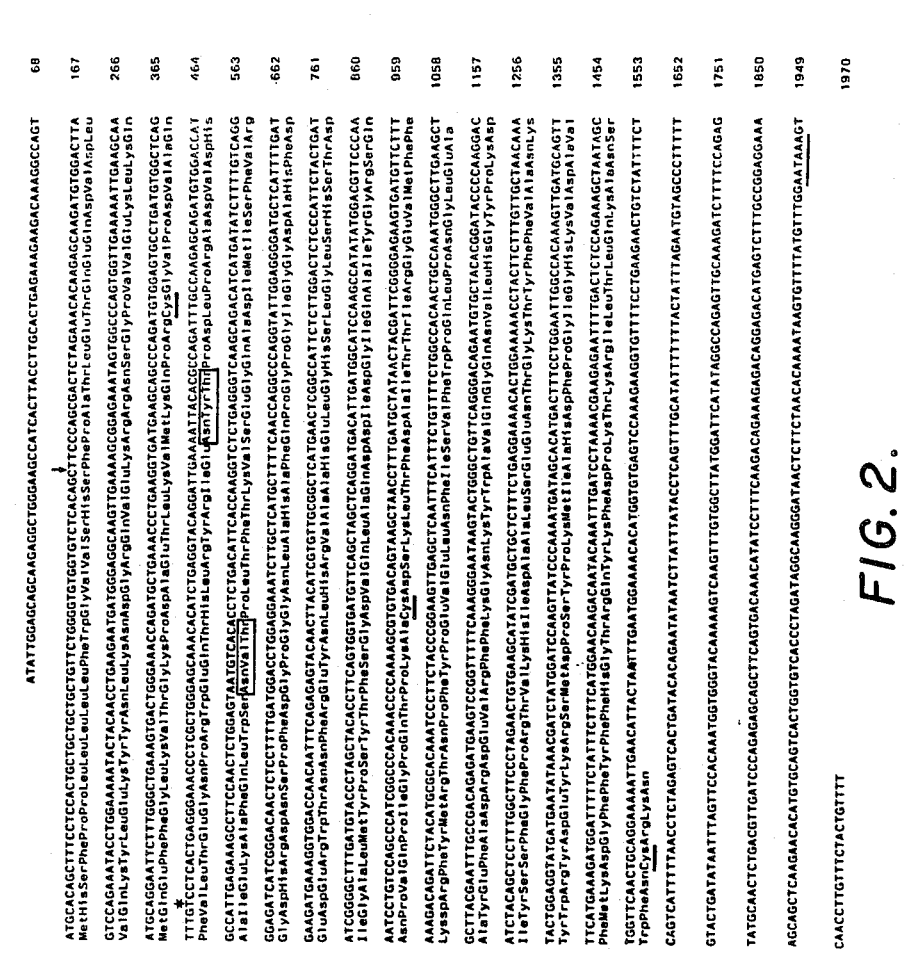

The top line represents the amino acid sequence of human skin collagenase as based on the cDNA sequence (FIG. 2). The bottom line represents the predicted sequence of the homologous rat protein. Only the amino acids differing from human collagenase are shown at the corresponding positions. Four gaps are introduced as indicated to maximize the homology. A stop codon is encountered in the rat cDNA at a position corresponding to Arginine-467 in human collagenase.

FIG. 3

Restriction Enzyme Map of the Human Collagenase cDNA Clone pCol 185.2

The restriction enzyme map of the pCol 185.2 cDNA clone was constructed by digestion of the cDNA with well-known, standard restriction enzymes commercially available from New England Biolabs, Inc., Beverly, Me. The abbreviations of the restriction enzymes and their recognition sequences are in accordance with the company standard specifications and the listing in *Nucleic Acids Res.* 11, r135-r167 (1983). The restriction sites utilized for end labeling in the sequencing procedure are shown in FIG. 3.

It is seen from the above that the in vitro translation system, using mRNA prepared from WUN 80547 cells and reticulocyte lysate, yields a single immunoprecipitable band (FIG. 1a) of 54 kDa which does not co-migrate with either of the mature procollagenase species, apparently due to the presence of an uncleaved signal peptide.

It has been established according to the present invention that the amino terminal portions of both proteolytically activated forms of the enzyme have an identical amino acid sequence. Sequence analysis of the intact S-carboxymethylated human skin procollagenase indicated that the amino-terminus was blocked. Both the 57 and 52 kDa proenzyme forms can be activated by limited digestion with trypsin generating their respective 47 and 42 kDa active enzyme forms. To determine the amino terminal protein sequence of these polypeptides, a purified preparation of procollagenase was subjected to affinity chromatography on blue Sepharose ® as previously described by Stricklin et al., *Biochemistry* 17, 2331-2337 (1978). The fractions enriched for the minor 57 kDa and the major 52 kDa proenzyme species were pooled separately and subjected to trypsin activation. The activation products were then separated by NaDodSO$_4$/PAGE, electroblotted onto glass fiber filters, and subjected to amino acid sequence analysis. The amino terminal sequence of each of these polypeptides was found to be identical (Table I).

The identity of the amino terminal sequence of both the minor 47 kDa and the major 42 kDa activated enzyme species obtained after NaDodSO$_4$/PAGE separation also suggested that purified preparations of collagenase contain no major contaminating proteins. Therefore, further analysis of the primary structure of the proenzyme protein was undertaken. Six peptides resulting from cyanogen bromide cleavage and two peptides from digestion with trypsin were purified and sequenced (Table I). The cyanogen bromide peptide CN2 was reverse translated and a mixture of 32, 17 bases long oligonucleotides was synthesized. The sequence of this mixed probe SO3 (Table II) is complementary to an mRNA coding for the 3' proximal portion of the CN2 peptide.

Northern blot analysis of the mRNA prepared from human skin fibroblast cultures showed that the synthetic oligomer probe hybridized to a 2.5 kb mRNA specie (FIG. 1b). To determine whether this mRNA specie coded for the collagenase protein, it was shown that the mRNA hybridizable to SO3 also codes for the amino-terminal protein sequence shared by both enzyme forms (Table I). The SO3 oligomer was 5' end-labeled, annealed to a preparation of total skin fibroblast mRNA, and the hybrid subjected to the AMV (Avian myeloblastosis virus) reverse transcriptase catalyzed primer extension reaction. The single major reaction product (670 bases) was isolated from a polyacrylamide-urea denaturing gel and sequenced. The sequence of the SO3 extension confirmed the protein sequence of the upstream portion of the CN2 peptide and was used to synthesize an additional 17 bases long oligonucleotide probe, SO6 (Table II) complementary to the same mRNA and positioned 180 bases upstream. When this oligomer was utilized as a primer in a similar test, a single 435 bases long primer extension product was isolated, sequenced and shown to contain the coding sequence for the 8 amino-terminus proximal amino acids found in both activated enzyme forms. These data provide evidence that the single mRNA specie coding for the collagenase-derived peptide CN2 also codes for the amino-terminal sequence of both trypsin-activated enzyme forms.

Having identified the collagenase coding mRNA, a cDNA library was constructed from collagenase-producing, human skin fibroblast mRNA, by methodology essentially as described by Alexander et al., *Gene* 31, 79-89 (1984), and Okayama and Berg, *Mol. Cell. Biol.* 3, 280-289 (1983). The library represents $1.5 \times 10^6$ original cloning events, with 75-80% of the clones carrying inserts. The total library plasmid DNA was isolated and size fractionated on 1% agarose gel in a supercoiled form. Fractions containing inserts of at least 2 kb or greater were extracted from the gel and used to retransform the host bacteria. Twenty-two transformants, hybridizing to both probes SO3 and SO6, were purified. The DNA from these clones was analyzed for the size of the 5' proximal region of the insert. Clones were selected which had the longest DNA fragment between the EcoR1 site in the linker of the vector and the EcoR1 site positioned 270 nucleotides downstream from the 5' end of the mRNA predicted from the sequence of the SO6 primer extension product. The clone pCol 185.2 contains a 1970 bp insert excluding the oligo (G) and poly (A) tails. Northern blot analysis (FIG. 1b) showed that this clone hybridized to the same mRNA specie as probe SO3. It is of interest to note that the partial cDNA clone of rabbit synovial collagenase hybridizes to a similar size of rabbit mRNA. See Gross et al., *Proc. Natl. Acad. Sci. USA* 81, 1981-1985 (1984).

The complete sequence of the pCol 185.2 insert has been determined and confirmed on both strands (FIG. 2). The 3' end nucleotide of the probe SO6 was positioned 435 bp downstream from the 5' end of the insert. This is in good agreement with the size of the SO6 primer extension product (435 bases), indicating that the pCol 185.2 insert represents the full, or nearly full, sequence of human collagenase mRNA. The insert consists of a 68 bp 5' untranslated leader, followed by initiating ATG Met codon and 1407 nucleotides coding for a 469 amino-acid-long preprocollagenase protein of $M_r$54092. The coding sequence is followed by two TGA termination codons positioned in frame. The 3' untranslated region includes 492 bp between the first termination codon and the start of the poly (A) tail, with a putative poly (A) addition signal 463 bp downstream from the end of the coding sequence.

The sequence surrounding the initiating codon is in agreement with the PurNNATGNPur initiation consensus sequence (where Pur=purine and N=any base). See, Kozak, *Microbiol. Rev.* 47, 1-15 (1983). The stretch of 19 amino acids immediately following the initiating Met constitutes a typical hydrophobic core of the signal peptide. See, for example, Kyte and Doolittle, *J. Mol. Biol.* 157, 105–132 (1982). Although the precise position of the amino-terminus of the mature protein is unknown, the hydropathicity plot, in combination with signal peptide cleavage patterns, allows one to predict that the cleavage of the signal peptide occurs after Ser at position 19. See, for example, Von Heijne, *Eur. J. Biochem.* 133, 17–21 (1983). The mature collagenase proenzyme then has a predicted $M_r$ 51929.

When the proenzyme is subjected to limited digestion with trypsin, several inactive intermediates can be detected by means such as described by Stricklin et al., *Biochemistry* 22, 61–68 (1983). The completely activated enzyme is apparently the result of the removal of 81 amino acids from the amino-terminus of the mature proenzyme. This activated form of collagenase has a predicted $M_r$ 42570 which is in good agreement with the experimental value. See Stricklin et al., *Biochemistry*, 17, 2331–2337 (1978). The proenzyme contains three cysteine amino acids at positions 92, 272 and 466. The cysteine at position 92 is located 8 amino acids upstream from the amino-terminus of the trypsin-activated enzyme and is therefore removed upon proteolytic activation of the collagenase. Two possible N-glycosylation sites ($Asn^{120}$, $Asn^{143}$) are contained within the trypsin activated $M_r$ 42570 enzyme specie.

The comparison of the pCol 185.2 cDNA sequence with the GenBank(®) nucleic acid sequences data base did not reveal any substantial homologies. A sequence of mRNA from rat skin fibroblasts, recently reported by Matrisian et al., supra, shares extensive homology with the coding sequence of the pCol 185.2 cDNA clone. The alignment of the protein sequences predicted from these clones is presented in Table III. The overall amino acid homology of the two proteins is 48%. The sequence proximal to the amino termini of both proteins is poorly conserved. The longest highly conserved region (positions 90–261) has 60.8% homology. The region between amino acids 261 and 288 is significantly divergent, and includes a 9 amino acid insertion. The carboxy terminus proximal region of the proteins share 46.4% homology over a length of 181 amino acids (positions 288–469). The rat protein contains a single potential N-glycosylation site. This site is in alignment with one of the sites ($Asn^{120}$) in the collagenase protein. Three out of four cysteine residues in the rat protein are conserved in human collagenase. The comparison of nucleic acid sequences of these cDNA clones in the coding region (data not shown) is in good agreement with the alignment presented in Table III. The 5' untranslated regions are of similar size (59 bp rat, 68 bp human) and show no significant conservation of sequence. The 3' untranslated region of human collagenase mRNA (469 bp) is longer than that of the rat (289 bp) and is significantly more divergent (39.5% homology) than the coding region.

Various other examples will be apparent to the person skilled in the art after reading the instant disclosure without departing from the spirit and scope of the invention and it is intended that all such examples be included within the scope of the appended claims.

What is claimed is:

1. Human skin fibroblast collagenase cDNA clone pCOL 185.2, containing a 1970 basepair insert and characterized as shown by the restriction map in FIG. 3 of the drawings.

2. The cDNA encoding for human skin fibroblast collagenase enzyme having the nucleotide sequence as shown in FIG. 2 of the drawings.

3. The cDNA comprising a 1407 basepair insert which codes for a 469 amino acid human skin fibroblast collagenase.

* * * * *